United States Patent [19]

Shinozaki et al.

[11] Patent Number: 4,748,327

[45] Date of Patent: May 31, 1988

[54] METHOD OF INSPECTING MASKS AND APPARATUS THEREOF

[75] Inventors: Toshiaki Shinozaki; Sadao Sasaki, both of Yokohama, Japan

[73] Assignee: Kabushiki Kaisha Toshiba, Kawasaki, Japan

[21] Appl. No.: 871,792

[22] Filed: Jun. 9, 1986

[30] Foreign Application Priority Data

Jun. 13, 1985 [JP] Japan .................. 60-128766

[51] Int. Cl.$^4$ .................. G01F 23/00; H01J 37/30
[52] U.S. Cl. .................. 250/358.1; 250/492.2
[58] Field of Search .................. 250/372, 373, 492.2, 250/492.22, 492.24, 492.3, 358.1, 361 R, 370 R

[56] References Cited

U.S. PATENT DOCUMENTS 4,572,956  2/1986  Tojo et al. .................. 250/492.2
4,608,332  8/1986  Ward .................. 250/492.24

FOREIGN PATENT DOCUMENTS 0083408  11/1982  European Pat. Off. .
60-098342  1/1985  Japan .
60-083941  5/1985  Japan .

OTHER PUBLICATIONS

IEEE Transactions on Electron Devices, vol. ED-22, No. 7, 7th Jul. 1975, pp. 409–413, New York, U.S.; J. P. Scott: "An Electron Image Projector with Automatic Alignment".
Proc. of SPIE vol. 334, p. 208, "Reticle Inspection Technology to Compare the Pattern Against Data", D. Awamura, 1982.
Proc. of SPIE vol. 334, p. 216, "Automatic Mask and Reticle Inspection System", H. Yang, 1982.
"Television by Electron Image Scanning", by Philo Taylor Farnsworth; pp. 411–444.

Primary Examiner—Janice A. Howell
Attorney, Agent, or Firm—Oblon, Fisher, Spivak, McClelland & Maier

[57] ABSTRACT

A method of inspecting masks which have lithographic patterns thereon, comprises the steps of depositing an electron-emissive layer on the patterned first major surface of the mask, the electron-emissive layer on the clear area of the patterned surface emitting electron beams when irradiated with energy beams, applying energy beams to the patterned surface from behind through the second major surface of the mask, guiding the electron beams emitted from the electron-emissive layer to an electron optical system, thereby forming an electron beam image of the pattern on a detector means, and comparing detection signals corresponding to the pattern and output by the detector means with reference signals representing the design shape and size of the pattern, thereby to inspect the mask.

15 Claims, 3 Drawing Sheets

METHOD OF INSPECTING MASKS AND APPARATUS THEREOF

BACKGROUND OF THE INVENTION

The present invention relates to a method of inspecting masks used in manufacturing LSI or the like, and also to an apparatus for performing the method.

Conventionally, to inspect the pattern formed on a photomask or the like, light having a wavelength of 0.4–0.7 μm is applied to one major surface of the mask, and the amount of light passing through the mask is detected. Since the amount of light changes according to the shape of the pattern, the presence or absence of the pattern and the dimensional accuracy of the pattern can be determined from the detected amount of light.

In practice, the mask is positioned in a plane which is perpendicular to the light beam, and is moved parallel to the plane while the light is being applied to it. The amount of the light passing through the mask is detected, and a first signal (i.e., detection signal) is generated from the detected amount of light. The first signal is compared with a second signal (i.e., reference signal) obtained from the design data used in forming the pattern. This conventional method is disclosed in Daikichi Awamura, *Reticle Inspection Technology to Compare the Pattern against Data*, Proc of SPIE, Vol., 334, 1982, p. 208.

With the method it is impossible to detect the pattern defects of less than about 1 μm, due to the interference or diffraction of light. This limited accuracy of inspection is sufficient in the photo-optical reduction exposure system, generally called stepper, which reduces and projects a mask image about one-fifth to one-tenth the original mask size onto a wafer.

The recent trend is that ultra LSI having wires less than 1 μm broad are developed. It is now expected that X rays, electron beams or ion beams are used to transfer a pattern to a wafer in the process of manufacturing ultra LSI. The conventional reduction transfer of the pattern image can no longer be applied, and the unit magnification pattern must be transferred to the wafer. Hence, the pattern defects must be detected and corrected to the accuracy of 0.1–0.2 μm. The conventional method of inspecting masks and patterns, which uses a light beam, can not obtain such high-accuracy detection of pattern defects.

SUMMARY OF THE IVENTION

One object of the invention is to provide a method of inspecting masks, which can detect minute defects or dimensional errors to the accuracy of less than 1 μm.

Another object of the invention is to provide an apparatus for inspecting masks, which can detect minute defects or dimensional errors to the accuracy of less than 1 μm.

According to the invention, there is provided a method for inspecting masks each having lithographic patterns thereon and having two major surfaces, which comprises the steps of:

depositing an electron-emissive layer on the patterned first major surface of the mask, said electronemissive layer on the clear area of the patterned surface emitting electron beams when irradiated with energy beams;

applying energy beams to said patterned surface from behind through the second major surface of the mask;

guiding the electron beams emitted from said electron-emissive layer to an electron optical system, thereby forming an electron beam image of said pattern on a detector; and comparing detection signals corresponding to the pattern and output by the detector with reference signals representing the design shape and size of the pattern, thereby to inspect the mask.

Moreover, according to the invention, there is provided an apparatus for inspecting masks which have lithographic patterns thereon, comprising:

a radiation source for applying an energy beam to the patterned first major surface of said mask from behind through the second major surface of said mask and an electron-emissive layer covering the patterned surface, thereby to cause said electron-emissive layer on the clear area of the pattern to emit electron beams;

means for forming an electron beam image of said pattern with the electron beams emitted from said electron-emissive layer;

detector means for receiving the electron beam image and generating detection signals from the electron beam image;

means for storing reference signals representing the design shape and size of the pattern;

means for comparing the detection signals with the reference signals, thereby to determine the features of the mask; and means for changing the position of the electron beam image of the pattern, which is formed on said detector means.

In the present invention, electron beams are used instead of light, to detect the pattern defects of masks. Therefore, the method and apparatus of the invention encounter neither diffraction of light nor interference of light which would degrade the accuracy of detecting the pattern defects. According to the present invention, the size and defects of the pattern can be detected in high accuracy of a submicron or less, in which the conventional method and apparatus can not be achieved. Hence, the method and apparatus can reliably inspect masks designed for use in transferring pattern images to wafers by using X rays or electron beams. Furthermore, when masks for photocathode projection are detected, which need to be provided with a photoelectric layer, the method and apparatus can inspect features of the photoelectric layer, too.

BRIEF DESCRIPTION OF THE DRAWINGS

Other objects and advantages of the invention will be apparent from the following description taken in conjunction with the accompanying drawings, in which:

FIG. 4 is a diagram schematically illustrating how the method of this invention is applied.

DETAILED DESCRIPTION OF THE PREFERRED EMBODIMENTS

The embodiments of the invention will now be described with reference to the drawings attached hereto.

Figure 1:
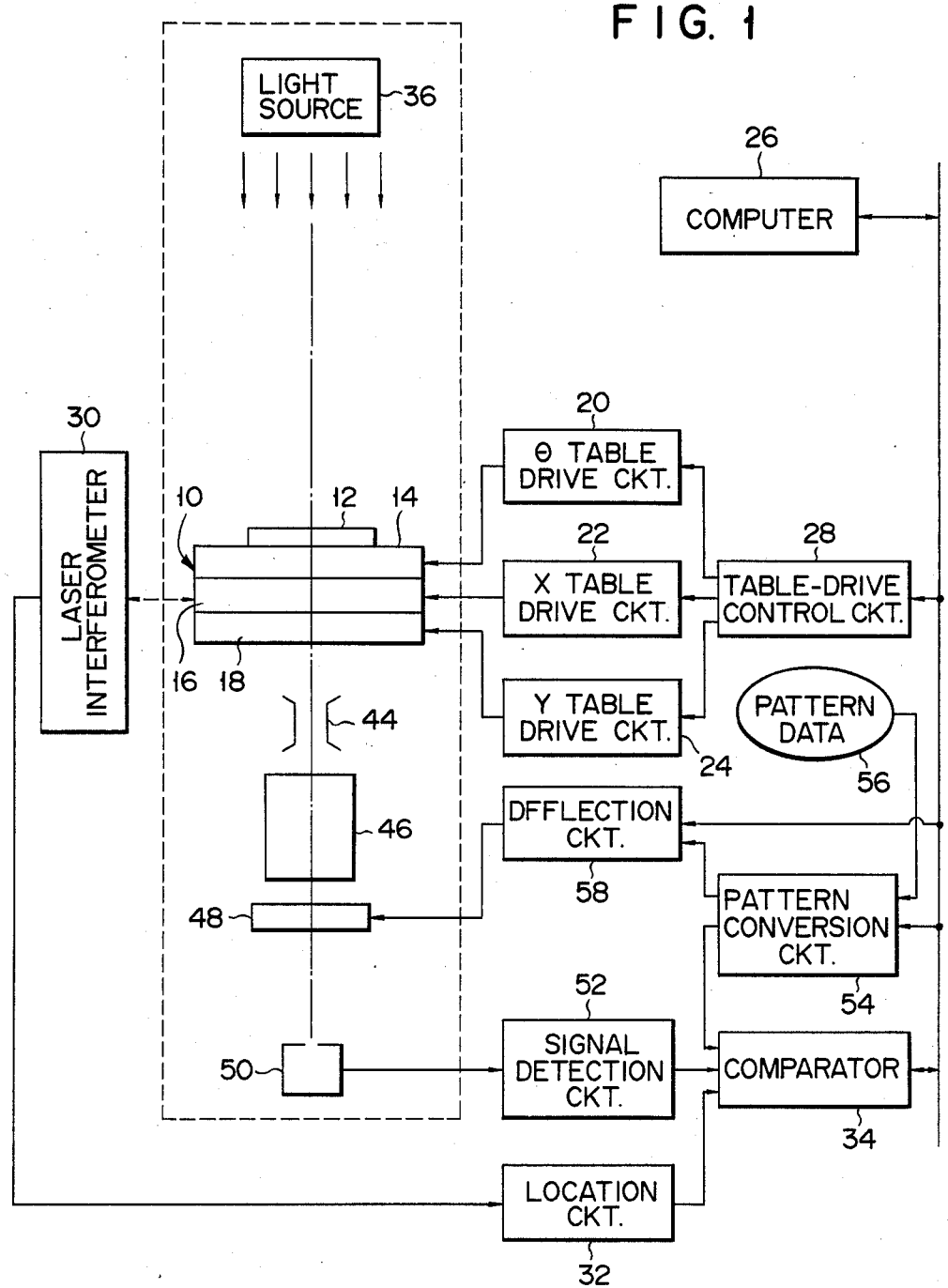
FIG. 1 is a block diagram schematically showing a mask defect inspecting apparatus according to one embodiment of the present invention.

FIG. 1 schematically shows an apparatus of this invention. As shown in this figure, the apparatus has table unit 10, on which mask 12 to be inspected is placed. The mask 12 has lithographic patterns thereon. Table unit 10 comprises θ table 14, X table 16 and Y table 18. The θ table can rotate. X table 16 can move in X direction (left to right and vice versa, in FIG. 1). Y table 18 can move in Y direction (back and forth, in FIG. 1). Tables 14, 16 and 18 are driven by signals supplied from θ table driving circuit 20, X table driving circuit 22 and Y table driving circuit 24, respectively. Circuits 20, 22 and 24 are controlled by table drive control circuit 28 which operates in accordance with the instructions supplied from computer 26. The position of table unit 10 is detected by laser interferometer 30. The output data of interferometer 30 is converted into an electrical signal by location circuit 32. The electrical signal is input to comparator 34.

Light source 36 for emitting ultraviolet rays is located above table unit 10. The ultraviolet rays, or an energy beam, emitted by light source 36 is applied to mask 12 put on table unit 10.

Figure 2:
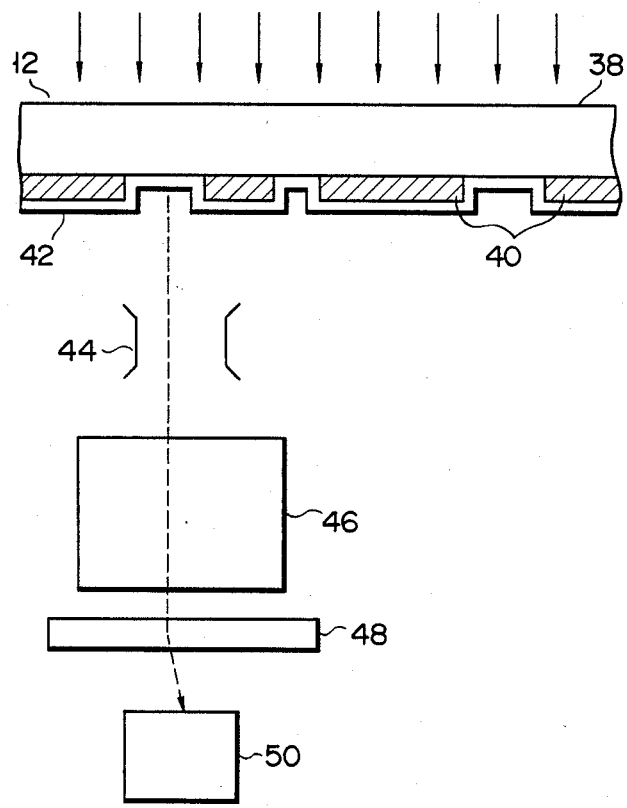
FIG. 2 is a cross-sectional view of the mask to be inspected by the apparatus shown in FIG. 1.

Mask 12 is designed for use in electron beam image transfer. As illustrated in FIG. 2, the mask comprises synthetic quartz plate 38, chromium pattern layer 40 deposited to the lower surface of plate 38, and photoemissive layer 42 covering pattern layer 40 and the lower surface of plate 38. Photoemissive layer 42 emits photoelectrons when illuminated with ultraviolet rays. Hence, layer 42 emits electron beams in accordance with the shape of the pattern 40.

The electron beams emitted from that portion of photoemissive layer 42 which corresponds to the inspected portion of mask 12 are accelerated by acceleration electrodes 44 to gain predetermined energy. The accelerated electron beams are guided through magnification electron optical system 46 and deflector 48 to detector 50. Therefore, a magnified electron beam image of the inspected portion of mask 12 is formed on detector 50. Detector 50 is a scintillator or a semiconductor detector comprising a P-N junction. The output signals of detector 50 are detected by signal detection circuit 52. Circuit 52 can output a signal corresponding to a small area of mask 12, when the electron beams are deflected by deflector 48. Deflector 48 is driven by deflection circuit 58 which in turn is controlled by computer 26 and pattern conversion circuit 54. Circuit 54 generates reference signals based on pattern data 56 which has been used in designing pattern 40.

As the θ table, X table and Y table of table unit 10 are rotated and moved, and the electron beams emitted from layer 42 are processed as described above, signal detection circuit 52 generates the signals representing the shape and size of entire pattern 40.

The output signals of signal detection circuit 52 are supplied to comparator 34. The reference signals which pattern conversion circuit 54 has generated from design pattern data 56 are input also to comparator 34. Comparator 34 compares the output signals of circuit 52 and the reference signals, based on the location signals supplied from location circuit 32. The results of the comparison are supplied to computer 26. Computer 26 analyses the results, thereby measuring the size of pattern 40 and detecting pattern defects, if any.

Figure 3:
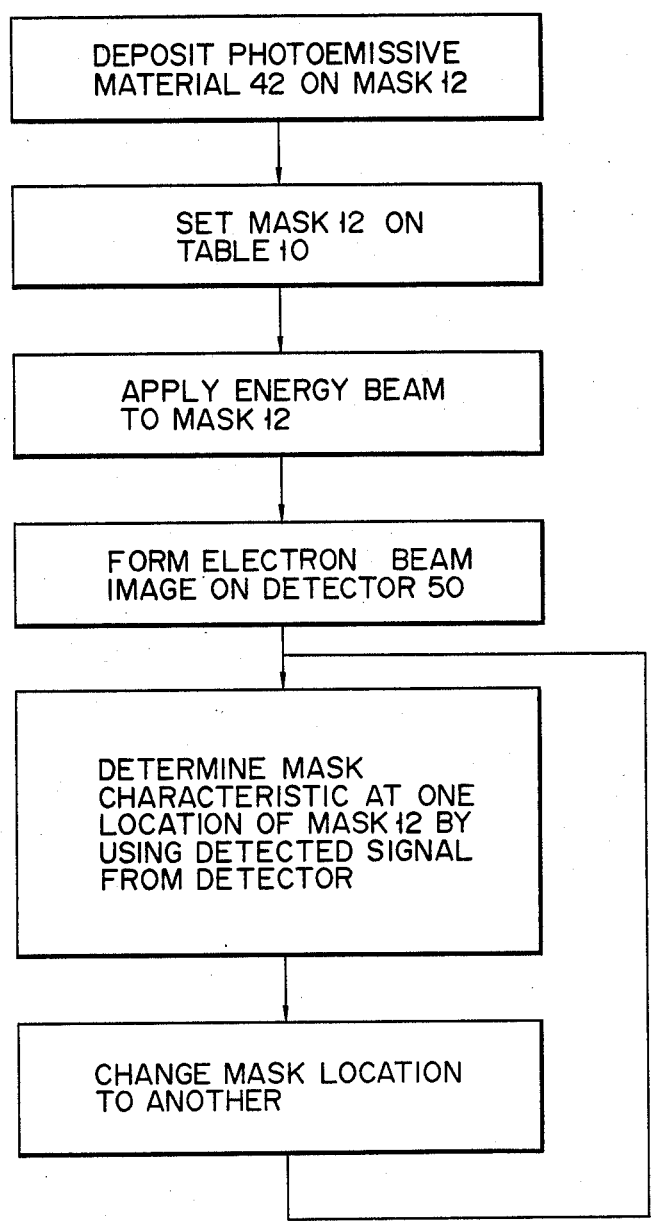
FIG. 3 is a flow chart explaining a mask defect inspecting method according to the invention.

With reference to FIGS. 3 and 4, the method of this invention, which employs the above apparatus to inspect masks, will be explained.

First, mask 12 with lithographic pattern 40 formed on one major surface is prepared. Then, photoemissive layer 42 of CsI is formed by vapor-deposition on said major surface of mask 12, thereby covering up pattern 40. (The step of forming layer 42 is, of course, unnecessary if the mask to be inspected is one for use in photocathode projection. The reason is that the photoemissive film 42 is formed in advance.) Photoemissive layer 42 has a thickness of 5 to 20 nm. Since layer 42 is so thin, it will cause no problems unless it is peeled off when mask 12 is used to manufacture LSI or the like. Needless to say, after the inspection of mask 12, layer 42 can be peeled off if it is no longer necessary.

Mask 12 is placed on θ table 14 of table unit, with the pattern-provided surface directed downward.

Ultraviolet rays are applied from light source 36 to the upper surface of mask 12. The ultraviolet rays impinging pattern 40 do not reach photoemissive layer 42, whereas those rays not impinging pattern 40 reaches layer 42. Those portions of layer 42 which receive ultraviolet rays emit electron beams, the distribution of which represents the shape and size of pattern 40 which is formed on synthetic quartz plate 38.

The electron beams emitted from that portion of photoemissive layer 42 which corresponds to the inspected portion of mask 12 are accelerated by electrodes 44 and gain predetermined energy. The accelerated electron beams are guided through magnifying electron optical system 46 and deflector 48 to detector 50, thereby forming a magnified image of the inspected portion of mask 12 on detector 50. In other words, part of the electron beams emitted from layer 42 which has been excited by the ultraviolet rays are applied to detector 50.

Thereafter, deflector 48 is operated, deflecting electron beams in Y direction, X table 16 is moved continuously in X direction, and Y table 28 is intermittently in Y direction. As a result, signal detection circuit 52 generates signals representing the magnified image of entire pattern 40. Comparator 34 compares these signals with the reference signals, as in the conventional mask inspection apparatuses. The results of the comparison are supplied to computer 26. Computer analyses the results, thereby determining whether or not masks 12 has defects—more precisely, whether or not pattern 40 is deformed or different in size from the design pattern.

In the present invention, what are emitted from mask 12 to be inspected are electrons, not light. Since electron beams neither interfere nor diffract, the accuracy of inspection can be very high even when a large magnification imaging is formed on detector 50. The results of the experiments conducted by the inventors hereof show that the apparatus and method according to the invention could detect not only mask deffects of less than 1 μm but also mask size errors of less than 0.1 μm. Both the apparatus and method can, therefore be effectively used also in inspecting masks designed for X-ray image transfer and electron beam image transfer. When the apparatus and method are employed to inspect masks for photocathode projection, they can inspect the overall characteristics of the pattern of the mask including the photoelectric layer thereof.

The apparatus of the invention is simple in structure. It comprises a optical mask inspecting apparatus of the known type and magnifying electron optical system 46 including deflector 48. Therefore, it can be easily realized.

The present invention is not limited to the embodiments described above. Instead of ultraviolet rays, X rays, electron beams, ion beams or the other energy beams can be used as energy beams, in which case light source 36 must be replaced by an X-ray source, electron source, ion source or the other energy source. Hence, if this is the case, the layer formed on the pattern-provided surface of the mask need not be a photoemissive layer. Any other layer that emits electrons when excited by energy beam can be used.

Furthermore, the structure of the apparatus is not limited to that illustrated in FIG. 1. For example, it can comprise an electron beam transfer apparatus of known type, a detection system (including detector 50 and signal detection circuit 52) and a data analyzing system (including comparator 34, pattern conversion circuit 54 and location circuit 32).

What is claimed is:

1. A method of inspecting a mask which has a lithographic pattern thereon, comprising the steps of:
    depositing an electron-emissive layer on a front surface of said mask on which said pattern is formed, said electron-emissive layer emitting electron beams when a rear surface of said mask is irradiated with energy beams;
    applying said energy beams to said electron-emissive layer through said rear surface of said mask to cause said electron beams to emit from said electron-emissive layer;
    guiding said electron beams emitted from said electron-emissive layer to an electron optical system, thereby forming an electron beam image of said pattern on a detector means;
    detecting said electron beam image by said detector means to generate detection signals; and
    comparing said detection signals corresponding to said pattern with reference signals representing a desirable shape and size of said pattern, thereby to inspect said mask.

2. The method according to claim 1, wherein said energy beams are ultraviolet rays, and said electron-emissive layer is made of CsI.

3. The method according to claim 1, wherein said electron optical system is magnifying electron optical system.

4. The method according to claim 1, wherein said detector means is a scintillator.

5. The method according to claim 1, wherein said detector means is a semiconductor detector.

6. The method according to claim 1, further comprising the step of controlling the position of the electron beam image formed on said detector means by deflecting said electron beams.

7. The method according to claim 1, wherein said guiding step comprises the steps of:
    guiding said electron beams emitted from said electron-emissive layer to said electron optical system; and
    magnifying said electron beams to form a magnified electron beam image of said pattern on said detector means.

8. An apparatus for inspecting a mask which has a lithographic pattern thereon, comprising:
    a radiation source for applying energy beams to an electron-emissive layer covering said pattern, which is formed on a front surface of said mask, through a rear surface of said mask, thereby to cause said electron-emissive layer to emit electron beams;
    means for forming an electron beam image of said pattern from said electron beam emitted from said electron-emissive layer;
    detector means for receiving said electron beam image and generating detection signals from said electron beam image;
    means for storing reference signals representing a desired shape and size of said pattern;
    means for comparing said detection signals with said reference signals, thereby to determine a feature of said mask; and
    means for changing a position of said electron beam image of said pattern, which is formed on said detector means.

9. The apparatus according to claim 8, wherein said radiation source is an ultraviolet ray lamp.

10. The apparatus according to claim 8, wherein said electron-emissive layer is made of CsI.

11. The apparatus according to claim 8, wherein said electron-emissive layer has a thickness of 5 to 20 nm.

12. The apparatus according to claim 8, wherein said detector means is a scintillator.

13. The apparatus according to claim 8, wherein said detector means is a semiconductor detector.

14. The apparatus according to claim 8, further comprising deflection means for deflecting said electron beams, thereby to control the position of the electron beam image formed on said detector means.

15. The apparatus according to claim 8, wherein said means for forming said electron beam image comprises:
    means for magnifying said electron beams to form a magnified electron beam image of said pattern.

* * * * *